(12) United States Patent
Viljoen

(10) Patent No.: US 11,155,773 B2
(45) Date of Patent: Oct. 26, 2021

(54) EXPEDITED PCR WITH STIRRING

(71) Applicant: NUtech Ventures, Lincoln, NE (US)

(72) Inventor: Hendrik Viljoen, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 535 days.

(21) Appl. No.: 16/072,932

(22) PCT Filed: Jan. 24, 2017

(86) PCT No.: PCT/US2017/014705
§ 371 (c)(1),
(2) Date: Jul. 26, 2018

(87) PCT Pub. No.: WO2017/132129
PCT Pub. Date: Aug. 3, 2017

(65) Prior Publication Data
US 2019/0040345 A1   Feb. 7, 2019

Related U.S. Application Data

(60) Provisional application No. 62/287,040, filed on Jan. 26, 2016.

(51) Int. Cl.
*C12M 1/10*       (2006.01)
*B01L 7/00*       (2006.01)
*C12M 1/34*       (2006.01)
*C12M 1/00*       (2006.01)
*C12Q 1/686*      (2018.01)
*C12Q 1/6806*     (2018.01)
*C12N 1/06*       (2006.01)

(52) U.S. Cl.
CPC .............. *C12M 1/10* (2013.01); *B01L 7/5255* (2013.01); *C12M 1/3476* (2013.01); *C12M 47/06* (2013.01); *C12Q 1/686* (2013.01); *B01L 2200/0668* (2013.01); *B01L 2300/1838* (2013.01); *B01L 2400/04* (2013.01); *B01L 2400/043* (2013.01); *C12N 1/066* (2013.01); *C12Q 1/6806* (2013.01)

(58) Field of Classification Search
CPC ...... C12M 1/10; C12M 1/3476; C12M 47/06; B01L 7/5255; B01L 2200/0668; B01L 2300/1838; B01L 2400/04; B01L 2400/043; C12Q 1/686; C12Q 1/6806; C12N 1/066
See application file for complete search history.

(56) References Cited

U.S. PATENT DOCUMENTS

| | | | |
|---|---|---|---|
| 6,165,778 A | 12/2000 | Kedar | |
| 6,649,419 B1 * | 11/2003 | Anderson | B03C 1/284 436/526 |
| 8,071,395 B2 * | 12/2011 | Davis | B03C 1/286 436/524 |
| 8,084,271 B2 * | 12/2011 | Korpela | B03C 1/286 436/177 |

(Continued)

*Primary Examiner* — William H. Beisner
*Assistant Examiner* — Danielle B Henkel
(74) *Attorney, Agent, or Firm* — Stinson LLP

(57) ABSTRACT

Disclosed are an apparatus and methods for rapid amplification of nucleic acids. More particularly, the present disclosure relates to an apparatus for mixing a reaction solution during amplification of nucleic acids and to methods for amplifying nucleic acids. Also disclosed are methods for lysing cells in a sample and amplifying nucleic acids.

17 Claims, 9 Drawing Sheets

(56) References Cited

U.S. PATENT DOCUMENTS

| | | |
|---|---|---|
| 8,133,671 B2 | 3/2012 | Williams et al. |
| 2009/0131650 A1 | 5/2009 | Brahmasandra et al. |
| 2010/0291536 A1 | 11/2010 | Viljoen et al. |
| 2011/0111978 A1* | 5/2011 | Boschetti ............ C07K 1/22 506/9 |
| 2013/0078641 A1 | 3/2013 | Viljoen et al. |
| 2014/0106386 A1* | 4/2014 | Umeno ............ B25J 9/0087 435/23 |

* cited by examiner

EXPEDITED PCR WITH STIRRING

CROSS-REFERENCE TO RELATED APPLICATIONS

This application claims priority to International Publication Number WO 2017/132129, filed on Jan. 24, 2017, which claims the benefit of U.S. Provisional Application Ser. No. 62/287,040, filed Jan. 26, 2016, the disclosures of which are hereby incorporated by reference in their entireties.

BACKGROUND OF THE DISCLOSURE

The present disclosure relates generally to an apparatus and methods for rapid amplification of nucleic acids. More particularly, the present disclosure relates to an apparatus for mixing a reaction solution during amplification of nucleic acids and to methods for amplifying nucleic acids.

Polymerase chain reaction (PCR) is a technology to amplify DNA copies of specific DNA or RNA fragments in a reaction chamber. PCR is extensively used in medicine, science, agriculture, veterinary medicine, food science, and environmental science. Isothermal amplification is an alternative approach to PCR that does not require changing the reaction temperature.

PCR is generally performed by repeated cycles of denaturation, annealing, and extension. In the denaturation step, a double-stranded DNA is separated into two single strands by heating. In the annealing step, primers bind to the complementary opposite strands. In the extension step, DNA polymerase extends the primer sequences to make copies of the template DNA.

PCR has been developed in various ways to improve detection efficiency and sensitivity. However, higher accuracy and sensitivity of PCR generally involves longer reaction times and higher costs. To improve the accuracy and sensitivity of PCR, methods have been developed for each step such as optimizing cycle time; and modifying reagents to minimize non-specific reactions and the development of sophisticated, high-performance devices. These adaptations lead to increases in total reaction time and higher costs.

Isothermal amplification techniques include, for example, loop mediated isothermal amplification (LAMP), helicase-dependent amplification, nicking enzyme amplification reaction, and recombinase polymerase amplification. LAMP amplifies target DNA at a constant temperature using either two or three primer sets and a polymerase with high strand displacement activity and replication activity. Helicase-dependent amplification uses a constant temperature and DNA Helicase, an enzyme that unwinds DNA, rather than cycling through denaturation and annealing/extension steps. Nicking enzyme amplification reaction amplifies DNA at a constant temperature using a polymerase and nicking enzyme. Recombinase polymerase amplification uses a recombinase, a single-stranded DNA-binding protein (SSB) and strand-displacing polymerase to specifically pair primers with double-stranded DNA to amplify the target DNA.

To improve the accuracy and sensitivity of PCR, methods have been developed for each step such as optimizing cycle time; modifying reagents to minimize non-specific reactions; and the development of sophisticated, high-performance devices. These adaptations lead to increases in total reaction time and higher costs. Alternative methods to PCR can require additional reagents and may be less versatile than PCR.

Accordingly, there exists a need to develop an apparatus and methods for improving nucleic acid amplification methods to quickly and accurately amplify nucleic acids.

SUMMARY OF THE DISCLOSURE

The present disclosure relates to an apparatus and methods for rapid amplification of nucleic acids. More particularly, the present disclosure relates to an apparatus for mixing a reaction solution during amplification of nucleic acids and to methods for amplifying nucleic acids.

In one aspect, the present disclosure is directed to an apparatus for conducting amplification of a nucleic acid comprising: a bit, wherein the bit is coupled to a system configured to apply rotational force to the bit; a reaction vessel comprising at least one reagent for amplifying a nucleic acid; and a measurement system configured to analyze a parameter of the reaction vessel.

In another aspect, the present disclosure is directed to a method of amplifying a nucleic acid in a sample, the method comprising: providing a reaction vessel comprising a nucleic acid and at least one reagent for amplifying the nucleic acid; inserting a portion of a bit into the reaction vessel, wherein the bit is coupled to a system configured to apply rotational force to the bit; and activating the system to rotate the bit for a sufficient time to amplify the nucleic acid.

In another aspect, the present disclosure is directed to a method for lysing a cell sample and amplifying a nucleic acid; the method comprising: transferring a sample comprising a cell to a cuvette, wherein the cuvette comprises a lysis buffer; adding a plurality of paramagnetic particles to the cuvette, wherein the plurality of paramagnetic particles comprises a coating for capturing a nucleic acid in the sample; inserting a portion of a bit into the lysis buffer, wherein the bit is coupled to a system configured to apply rotational force to the bit and coupled to magnetic element configured to apply a magnetic field to the bit; activating the magnetic element to apply the magnet field, resulting in the plurality of paramagnetic particles to contact the bit; transferring the plurality of magnetic particles to a reaction buffer; deactivating the magnetic element to release the plurality of paramagnetic particles from the bit; and activating the system to apply rotational force to the bit for a sufficient time to amplify the nucleic acid.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

Figure 1:
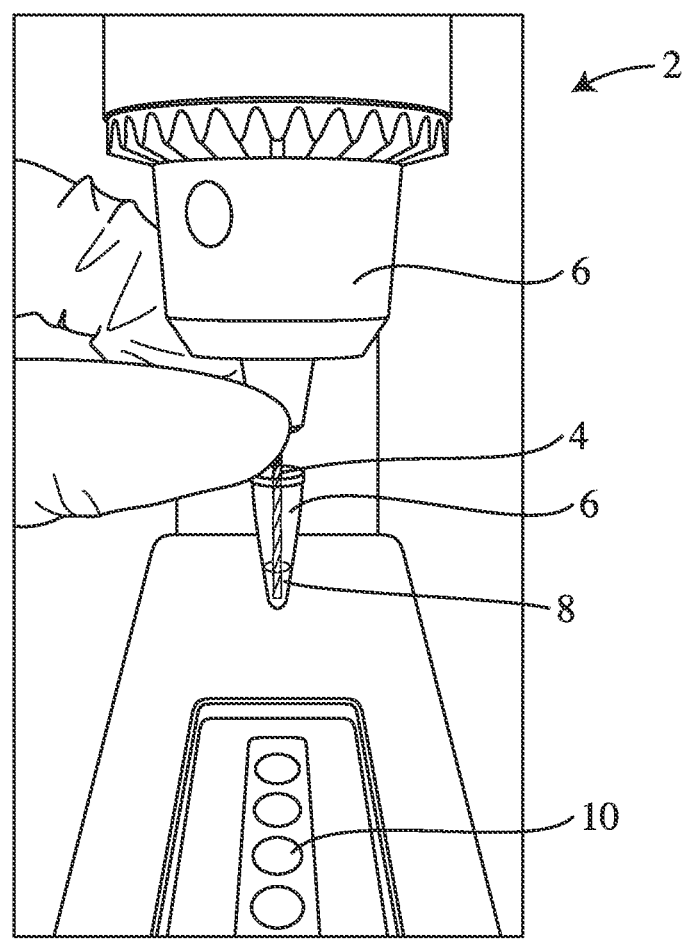
FIG. 1 is a side view of an embodiment using a drill press as the mechanism for rotating a bit. The cuvette is held out of the isothermal instrument to demonstrate the portion of the bit inserted into the reaction mixture.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, the preferred materials and methods are described below.

In accordance with the present disclosure, an apparatus and methods have been developed for amplifying a nucleic acid. The apparatus and methods include a bit and a system coupled to the bit configured to apply rotational force to the bit to provide constant stirring during the amplification reaction.

Apparatus

In one aspect, the present disclosure is directed to an apparatus for conducting amplification of a nucleic acid with continuous stirring. The apparatus includes: a bit, wherein the bit is coupled to a system configured to apply rotational force to the bit; a reaction vessel comprising at least one reagent for amplifying a nucleic acid; and a measurement system configured to analyze a parameter of the reaction vessel.

Exemplary apparatus 2 is shown in FIG. 1. Exemplary apparatus 2 includes bit 4 and a drill press 3 as the system (mechanism) for rotating bit 4. A portion of bit 4 is inserted in reaction vessel (e.g., cuvette) 6 below the surface of reaction mixture 8. In operation, reaction vessel (e.g., cuvette) 6 having bit 4 is placed in the reaction vessel (e.g., cuvette) holder of measurement system 10.

Any system for providing rotational force to the bit can be used. Suitable systems include motors to rotate the bit. Particularly suitable motors include, for example, electrical motors (e.g., BLADE motors; WALKERA motors; EACHINE motors), drill presses and handheld drills. In some embodiments, the system can be configured to control the speed (rotations per minute) of the bit. In other embodiments, the system can be a single speed mechanism having an on-off configuration.

The bit is coupled to a system for controllably rotating the bit. The system provides torque to rotate the bit. Rotation of the bit with bit geometry creates fluid motion. Without being bound by theory, continuous flow generated by rotation of the bit in the reaction mixture expedites assembly of the reaction components to reduce or eliminate mass transfer (or diffusion) of the components. Upon more rapid assembly of the components resulting from the constant stirring provided by rotation of the bit, amplification can proceed.

Suitable bits include, for example, bit configurations such as spade, lip and spur (brad point), masonry bit and twist drill bits. Particularly suitable bits include a non-smooth configuration or non-uniform configuration or varying profile configuration.

In embodiments using a twist drill bit configuration, the spiral (or rate of twist) in the bit produces radial and axial flow of the reaction solution. Twist drill bits can range in diameter from about 0.051 mm to about 4 mm.

Any length bit can be used that allows for inserting the bit proximate to the bottom of the reaction vessel without contacting the inner surface of the reaction vessel. The bit tip is positioned a desirable distance from the bottom of the reaction vessel such that its positioning does not optically interfere with apparatus embodiments including an optical reader as the optical signal is typically taken from the bottom of the reaction vessel.

Any material can be used for the bit. Particularly suitable material for the bit includes metal materials to which a magnetic field can be applied.

The apparatus can further include a detector for monitoring the amplification. A particularly suitable detector can be an optical detector.

Figure 2:
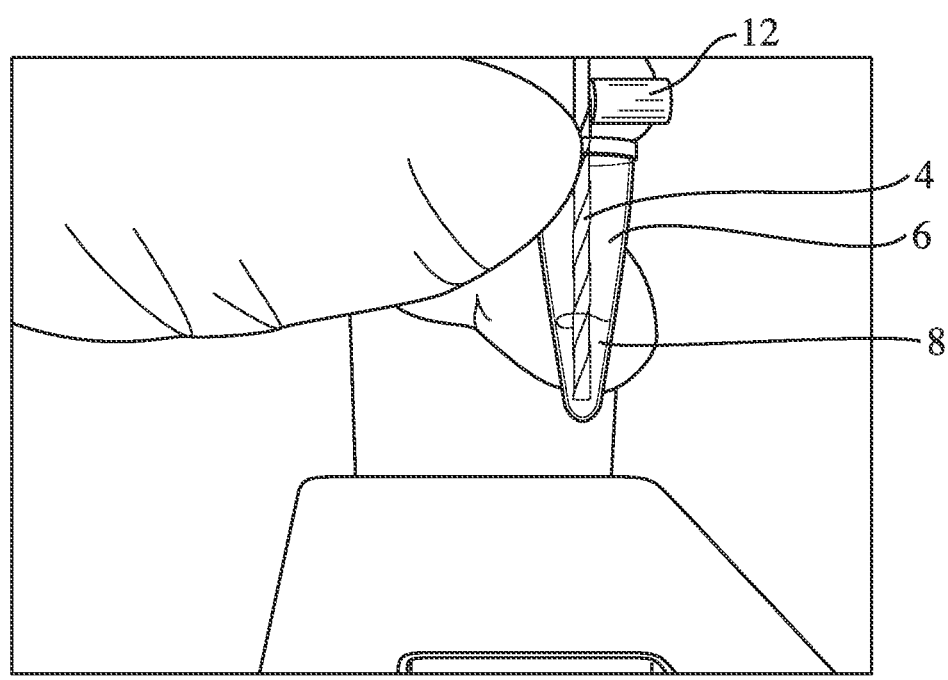
FIG. 2 is a side view of an embodiment having an external magnet contacted with a bit as a magnetic element for providing a magnetic field to capture super paramagnetic particles. The cuvette is held out of the isothermal instrument to demonstrate the portion of the bit inserted into the reaction mixture.

The apparatus can further include a magnetic element configured to apply a magnetic field to the bit. A suitable magnetic element includes an external magnet that is contacted with a bit made of a metal material. As shown in FIG. 2, an external magnet 12 can be contacted with a metal bit 4. Metal bit 4 is positioned within reaction vessel 6 with a portion of the metal bit 4 positioned below the surface of lysis buffer (or reaction mixture) 8. In embodiments using super paramagnetic particles, contacting magnet 12 to metal bit 4 provides a magnetic field allowing for the capture of super paramagnetic particles in the solution (for example, lysis buffer and reaction mixture).

The reaction vessel contains reagents for amplification. Reagents for amplification include, for example, nucleic acid template, buffer solution, deoxyribonucleotides (dNTPs) (adenine, guanine, cytosine, and thymine), oligonucleotide primers, polymerase, bivalent cations (e.g., magnesium or manganese), monovalent cations (e.g., potassium) and other components known to those skilled in the art. In embodiments for lysis, the reaction vessel can contain reagents for lysis. Reagents for lysis include, for example, buffers, detergents, protease inhibitors, chelators, nuclease inhibitors and other components known to those skilled in the art. Reagents for nucleic acid amplification and lysis can be obtained from commercial sources. The reagents can further be in the form of lypholized pellets which are reconstituted in water at the beginning of each experiment.

Suitable reaction vessels include cuvettes suitable for amplification reactions. Suitable reaction vessels include 0.1 mL and 0.5 mL PCR tubes for performing 10 μL to 200 μL reaction volumes. Suitable reaction vessels include cuvettes that allow for optical detection of amplification products.

Suitable speeds for rotating the bit can range from about 500 rpm to about 7,000 rpm. A particularly suitable speed is about 1,400 rpm.

The bit is continuously rotated at the start of the reaction (after all reagents are contained in the cuvette) until the optical signal reaches its plateau. Although less desirable, the bit rotation can be pulsed wherein the bit is rotated for a period of time, then stopped, then rotated for a second period of time. Pulsing can be performed any number of times.

The measurement system configured to analyze a parameter of the reaction vessel includes a light emitting diode. The measurement system can also include a detector. Suitable measurement systems include commercially available systems such as, for example, ESEQuant TS2 from QIAGEN.

A particularly suitable parameter analyzed using the measurement system includes fluorescence.

Amplification product production can be monitored by methods known to those skilled in the art. For example, amplification products can be monitored by electrophoresis using agarose gels and polyacrylamide gels. A particularly preferred method for monitoring amplification product production is by optical detection.

Optical detection of amplified product involves the use of nucleotides with a detectable label. Detectable labels include, for example, digoxigenin, biotin, fluorescent dyes, intercalating dyes and combinations thereof.

Optical detectors such as fluorimeters can be used for optical detection of amplified products.

Methods for Conducting Amplification with Continuous Stirring

In another aspect, the present disclosure is directed to a method for conducting amplification with continuous stirring of a reaction. The method includes: providing a reaction vessel comprising a nucleic acid and at least one reagent for amplifying the nucleic acid; inserting a portion of a bit into the reaction vessel, wherein the bit is coupled to a system configured to apply rotational force to the bit; and activating the system to rotate the bit for a sufficient time to amplify the nucleic acid.

In one embodiment, the bit is rotated continuously from initiation of the amplification until conclusion of the amplification. In another embodiment, the rotation can be pulsed wherein the bit is rotated for a period of time, then stopped, then rotated for a second period of time.

Suitable speeds for rotating the bit can be from about 500 rpm to about 7,000 rpm. A particularly suitable speed is about 1,400 rpm.

The method can further include monitoring the amplification Amplification product production can be monitored by methods known to those skilled in the art. For example, amplification products can be monitored by electrophoresis using agarose gels and polyacrylamide gels. A particularly preferred method for monitoring amplification product production is by optical detection.

Optical detection of amplified product involves the use of nucleotides with a detectable label. Detectable labels include, for example, digoxigenin, biotin, fluorescent dyes, intercalating dyes and combinations thereof.

Optical detectors such as fluorimeters can be used for optical detection of amplified products.

The reaction vessel contains reagents for amplification. Reagents for amplification include, for example, nucleic acid template, buffer solution, deoxyribonucleotides (dNTPs) (adenine, guanine, cytosine, and thymine), oligonucleotide primers, polymerase, bivalent cations (e.g., magnesium or manganese), monovalent cations (e.g., potassium) and other components known to those skilled in the art. Reagents for nucleic acid amplification can be obtained from commercial sources. The reagents can further be in the form of lyophilized pellets, which are reconstituted in water at the beginning of each experiment.

Any nucleic acid obtained from any sample source can be amplified according to the disclosed method. Examples of sample sources include bacteria, viral, fungal, plant and animal sources. Particularly, suitable samples can be, for example, saliva, sputum, blood, plasma, serum and a cheek swab. The samples can be further processed using methods known to those skilled in the art to isolate molecules contained in the sample such as, for example, cells, proteins and nucleic acids (e.g., DNA and RNA).

In some embodiments, the probe can be a labeled probe. Suitable labels can be, for example, a fluorescent label, an enzyme label, a radioactive label, a chemical label, and combinations thereof. Suitable radioactive labels are known to those skilled in the art and can be a radioisotope such as, for example, $^{32}P$, $^{33}P$, $^{35}S$, $^{3}H$ and $^{125}I$. A particularly suitable label can be, for example, SYBR® Green (commercially available from Life Technologies). A particularly suitable probe can be, for example, an oligonucleotide labelled with SYBR® Green. Suitable chemical labels can be, for example, periodate and 1-Ethyl-3-[3-dimethylaminopropyl] carbodiimide hydrochloride (EDC).

Suitable isothermal amplification assays include, for example, nucleic acid sequence-based amplification (NASBA), strand displacement amplification (SDA), loop-mediated amplification (LAMP), Invader assay, rolling circle amplification (RCA), signal mediated amplification of RNA technology (SMART), helicase-dependent amplification (HDA), recombinase polymerase amplification (RPA), nicking endonuclease signal amplification (NESA) and nicking endonuclease assisted nanoparticle activation (NEANA), exonuclease-aided target recycling (e.g., exonuclease III-aided target recycling), Junction or Y-probes, reactivation of enzymatic activity, ultrasensitive detection of microRNA, split peroxidase-like DNA enzyme probes (e.g., split DNAZyme and deoxyribozyme amplification strategies), template-directed chemical reactions that lead to amplified signals, non-covalent DNA catalytic reactions, hybridization chain reactions (HCR) and detection via the self-assembly of DNA probes to give supramolecular structures (see, Yan et al., Mol. BioSyst., 2014, 10, 970, which is incorporated by reference herein).

The sample can be any sample as known to those skilled in the art. Particularly suitable samples include, for example, a saliva sample, a blood sample, a serum sample, a plasma sample and a cheek swab.

Method for Lysing and Nucleic Acid Amplification

In another aspect, the present disclosure is directed to a method for lysing a cell sample and amplifying a nucleic acid. The method includes transferring a sample comprising a cell to a cuvette, wherein the cuvette comprises a lysis buffer; adding a plurality of paramagnetic particles to the cuvette, wherein the plurality of paramagnetic particles comprises a coating for capturing a nucleic acid in the sample; inserting a portion of a bit into the lysis buffer, wherein the bit is coupled to a system configured to apply rotational force to the bit and coupled to magnetic element configured to apply a magnetic field to the bit; activating the magnetic element to apply the magnet field, resulting in the plurality of paramagnetic particles to contact the bit; transferring the plurality of magnetic particles to a reaction buffer; deactivating the magnetic element to release the plurality of paramagnetic particles from the bit; and activating the system to apply rotational force to the bit.

Particularly suitable paramagnetic particles include superparamagnetic particles. Paramagnetic particles and superparamagnetic particles coated with a polymer bind nucleic acids in the lysis solution. Upon application of a magnetic field, the particles bind to the bit. The particles with bound nucleic acids are then transferred to a reaction vessel, where removal of the magnetic field results in release of the particles into the reaction mixture. The system for providing rotational force to the bit can then be activated.

In embodiments for lysis, the reaction vessel can contain reagents for lysis. Reagents for lysis include, for example, buffers, detergents, protease inhibitors, chelators, nuclease inhibitors and other components known to those skilled in the art. Reagents for nucleic acid amplification and lysis can be obtained from commercial sources. The reagents can further be in the form of lyophilized pellets which are reconstituted in water at the beginning of each experiment. Upon capture of the particles containing template nucleic acids from the lysis reaction, the lysis buffer can be removed and replaced with the amplification reaction mixture using the same cuvette. Alternatively, upon capture of the particles containing template nucleic acids from the lysis reaction, the particles on the bit can be transferred to a second reaction vessel containing amplification reagents. The reaction vessel contains reagents for amplification. Reagents for amplification include, for example, nucleic acid template, buffer solution, deoxyribonucleotides (dNTPs) (adenine, guanine, cytosine, and thymine), oligonucleotide primers, polymerase, bivalent cations (e.g., magnesium or manganese), monovalent cations (e.g., potassium) and other components known to those skilled in the art.

Suitable speeds for rotating the bit can be from about 500 rpm to about 7,000 rpm. A particularly suitable speed is about 1,400 rpm.

The method can further include monitoring the amplification Amplification product production can be monitored by methods known to those skilled in the art. For example, amplification products can be monitored by electrophoresis using agarose gels and polyacrylamide gels. A particularly preferred method for monitoring amplification product production is by optical detection.

Optical detection of amplified product involves the use of nucleotides with a detectable label. Detectable labels include, for example, digoxigenin, biotin, fluorescent dyes, intercalating dyes and combinations thereof.

Optical detectors such as fluorimeters can be used for optical detection of amplified products.

The sample can be any sample as known to those skilled in the art. The sample can be a bacterial sample, a viral sample, a fungal sample, a plant sample, and an animal sample. The sample can be a tissue, a tissue homogenate, and a cell culture, for example Particularly suitable samples include, for example, a saliva sample, a blood sample, a serum sample, a plasma sample and a cheek swab.

The disclosure will be more fully understood upon consideration of the following non-limiting Examples.

EXAMPLES

Example 1

In this Example, a wide range of rotation speeds (rpm's) were explored for amplification.

Specifically, the same DNA system was amplified while the bit was rotated at speeds from 540 rpm to 7,000 rpms. In all cases three repeats were done to show consistency. Recombinase Polymerase Amplification (RPA) was performed using the TWISTAMP® Basic kit, having a 50 μl volume (TwistDx Ltd., Cambridge, United Kingdom). Primers were set at a concentration of 10 μM as well as a 5× concentrated solution of SYBR® green and DNA at a concentration of 0.1 ng/μl, having approximately 13,200 copies. A master mix was made for each experiment, which was used to rehydrate a freeze-dried pellet from TwistDx Ltd. in a 0.2 μl reaction tube. Once all components were added, the tubes were vortexed and centrifuged; a solution of 280 nM Mg acetate was then pipetted into each reaction tube which was then immediately put into the tubescanner device. The reaction components were supplied by TwistDx Ltd. The fluorescent signal is in the FAM channel with 470 nm excitation and 520 nm detection. Each experiment was ran for 20 minutes at 39° C. The real-time readout was courtesy of TWISTA® Studio software, version 2.6.0 (TwistDx, Ltd.) which interpreted fluorescent data into graphs of Intensity (mV) vs. time (s). The control tubes had the same contents, the only difference is that the tubes were not stirred after being put into the thermal incubator.

Figure 3A:
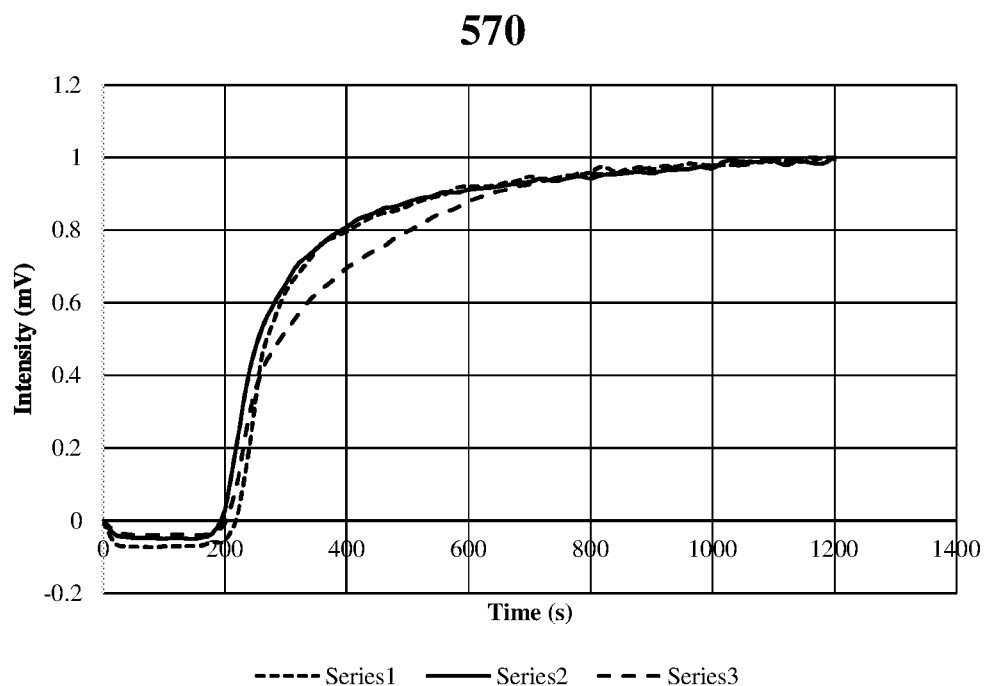
FIGS. 3A-3G are graphs depicting optical outputs at different reaction mixing speeds.
Figure 3B:
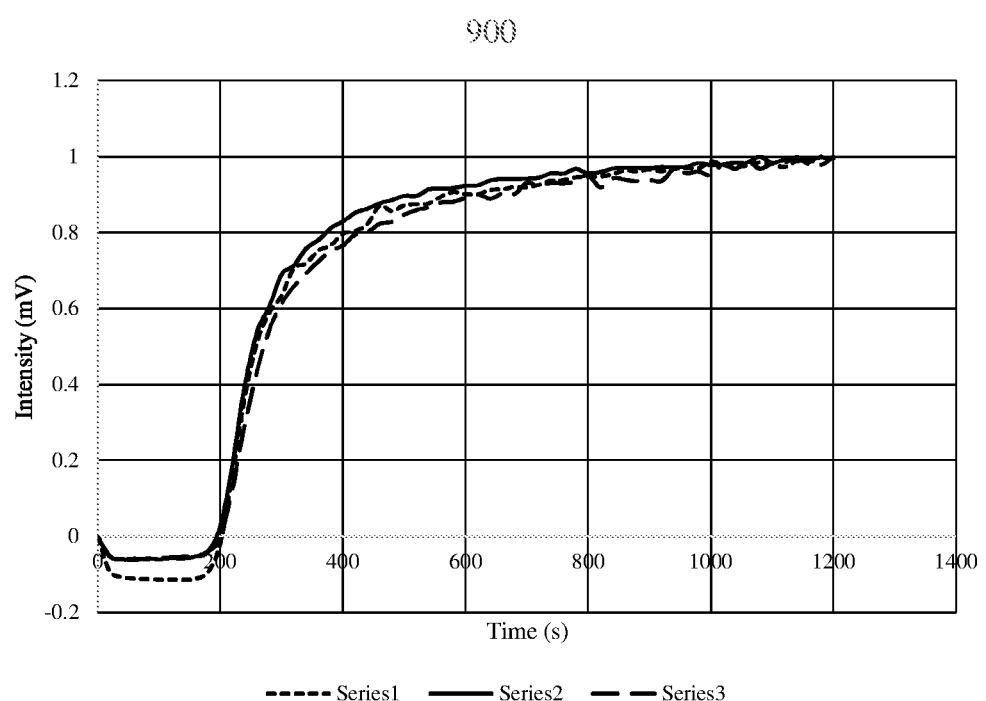
Figure 3C:
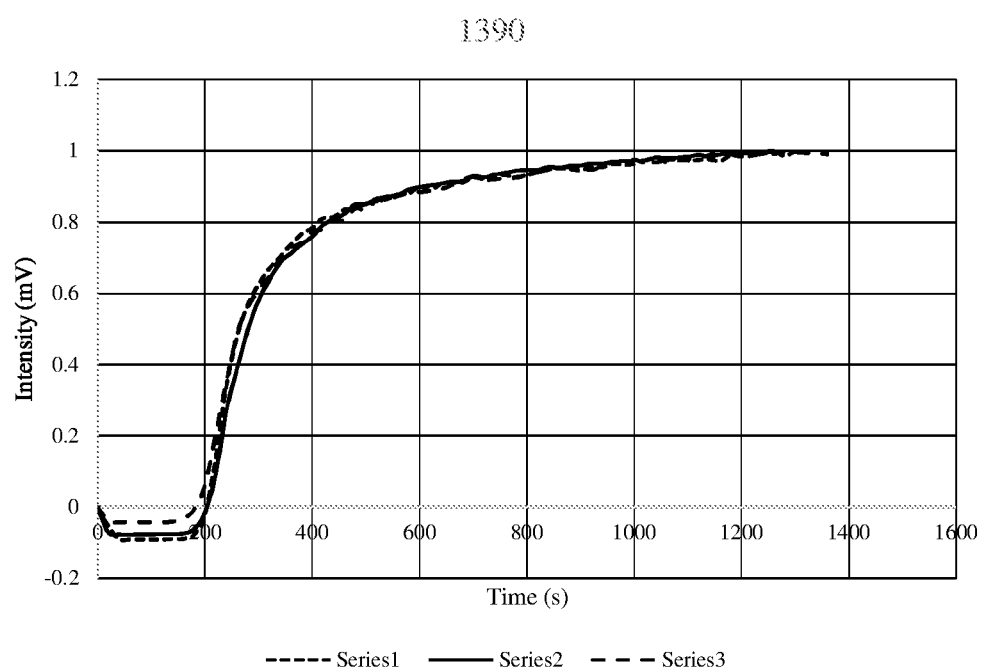
Figure 3D:
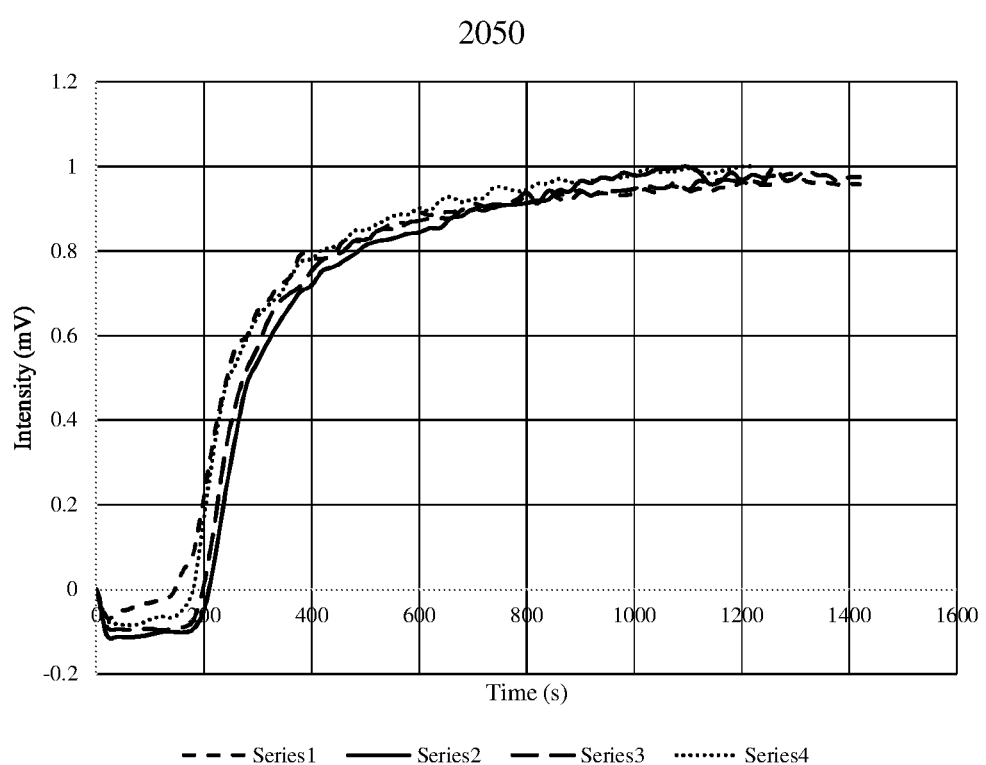
Figure 3E:
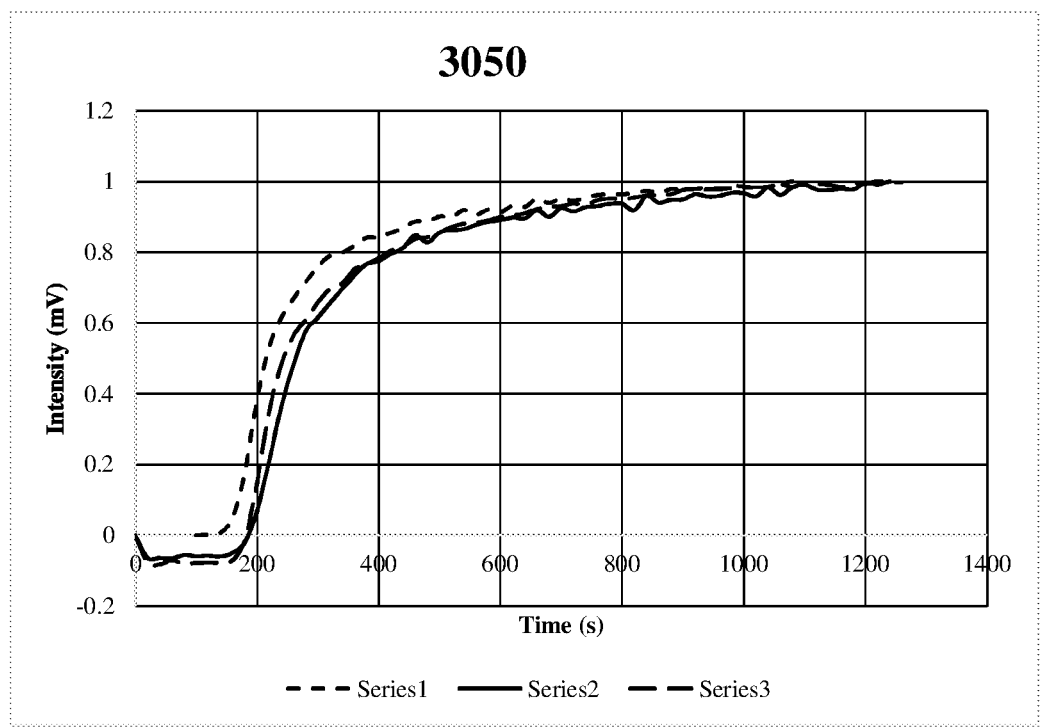
Figure 3F:
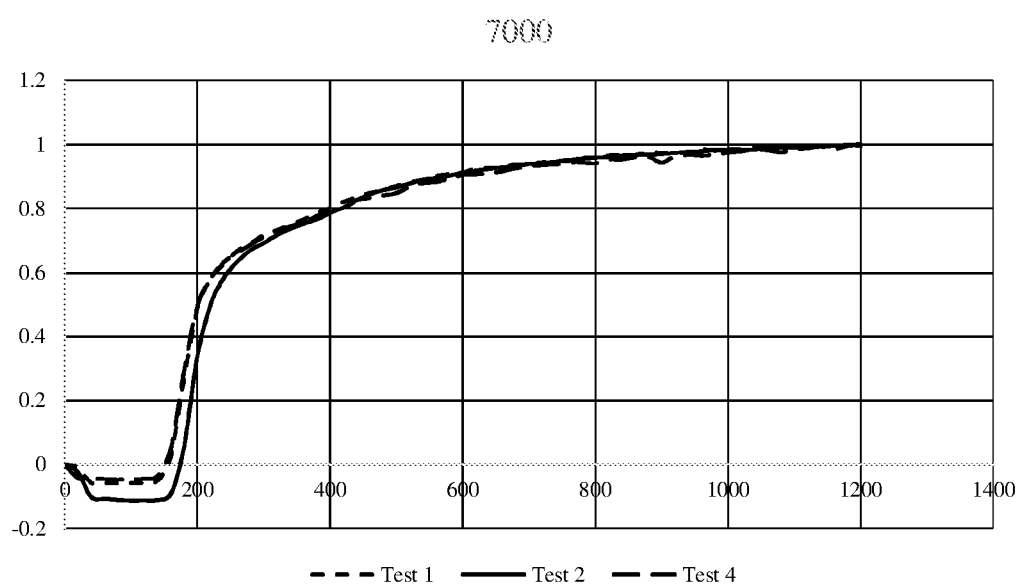
Figure 3G:
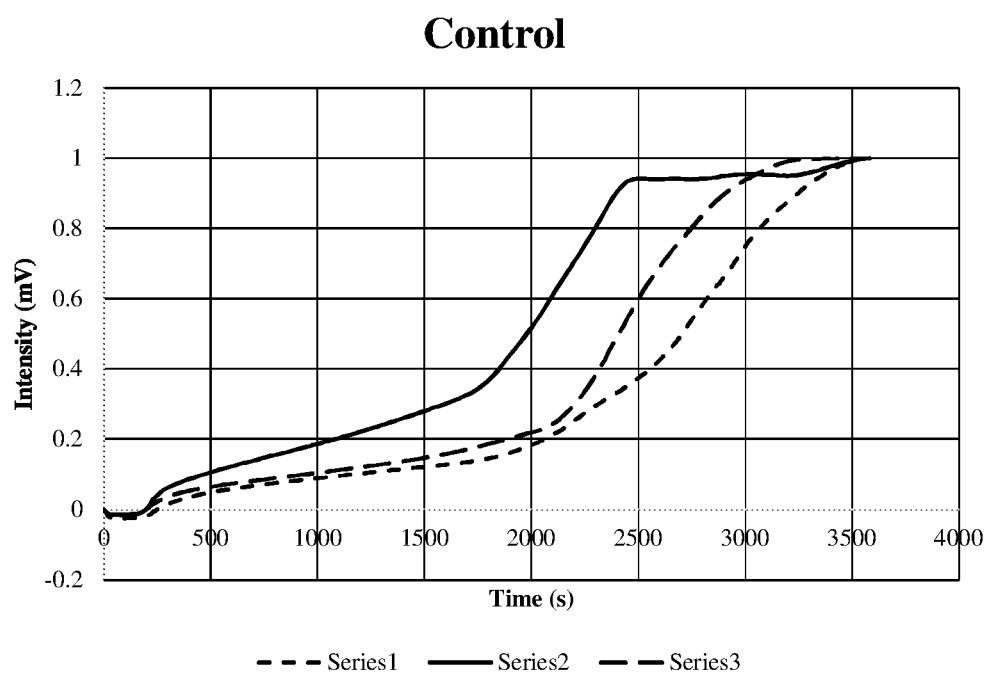

As shown in FIGS. 3A-3F, little differences were noted, although the system performed slightly faster at the top speed. FIG. 3G shows the amplification reaction performed with no stirring. When compared at the time where the signal starts to pick up, it took approximately 1500 seconds for detection of the amplification product in the non-stirred experiment and approximately 200-300 seconds for detection of the amplification product in the stirred experiments. These results demonstrate a five-fold improvement in the stirred experiments as compared to the non-stirred experiment.

In view of the above, it will be seen that the several advantages of the disclosure are achieved and other advantageous results attained. As various changes could be made in the above methods and systems without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. An apparatus for conducting amplification of a nucleic acid comprising:
   a bit, wherein the bit is coupled to a system configured to apply rotational force to the bit;
   a magnetic element that applies a magnetic field to the bit such that the bit is configured to capture one or more paramagnetic particles;
   a reaction vessel comprising at least one reagent for amplifying a nucleic acid; and
   a measurement system configured to analyze a parameter of the reaction vessel.

2. The apparatus of claim 1 wherein the measurement system comprises a light emitting diode.

3. The apparatus of claim 1 wherein the measurement system comprises a detector for monitoring the amplification.

4. The apparatus of claim 1 wherein the parameter is fluorescence.

5. A method of amplifying a nucleic acid in a sample, the method comprising:
   providing a reaction vessel comprising a nucleic acid and at least one reagent for amplifying the nucleic acid;
   inserting a portion of a bit into the reaction vessel, wherein the bit is coupled to a system configured to apply rotational force to the bit;
   applying a magnetic field to the bit such that the bit is configured to capture one or more paramagnetic particles; and
   activating the system to rotate the bit for a sufficient time to amplify the nucleic acid.

6. The method of claim 5, wherein the bit is rotated at a speed ranging from about 500 rpm to about 7,000 rpm.

7. The method of claim 5, further comprising monitoring the amplification.

8. The method of claim 7, wherein the monitoring comprises optical detection.

9. The method of claim 5, wherein the sample is selected from the group consisting of a saliva sample, a blood sample, a serum sample, a plasma sample and a cheek swab.

10. The method of claim 5, wherein the sample is selected from the group consisting of a bacterial sample, a viral sample, a fungal sample, a plant sample, and an animal sample.

11. A method for lysing a cell sample and amplifying a nucleic acid, the method comprising:

transferring a sample comprising a cell to a cuvette, wherein the cuvette comprises a lysis buffer;

providing a plurality of paramagnetic particles to the cuvette, wherein the plurality of paramagnetic particles comprises a coating for capturing a nucleic acid in the sample;

inserting a portion of a bit into the lysis buffer, wherein the bit is coupled to a system configured to apply rotational force to the bit and coupled to a magnetic element configured to apply a magnetic field to the bit;

activating the magnetic element to apply the magnet field, resulting in the plurality of paramagnetic particles to contact the bit;

transferring the plurality of magnetic particles to a reaction buffer;

deactivating the magnetic element to release the plurality of paramagnetic particles from the bit; and activating the system to apply rotational force to the bit for a sufficient time to amplify the nucleic acid.

12. The method of claim 11, wherein the reaction buffer comprises a reagent for amplification of a nucleic acid.

13. The method of claim 11, wherein the bit is rotated at a speed ranging from about 500 rpm to about 7,000 rpm.

14. The method of claim 11, further comprising monitoring the amplification.

15. The method of claim 14, wherein the monitoring comprises optical detection.

16. The method of claim 11, wherein the cell sample is selected from the group consisting of a saliva sample, a blood sample, a serum sample, a plasma sample and a cheek swab.

17. The method of claim 11, wherein the cell sample is selected from the group consisting of a bacterial sample, a viral sample, a fungal sample, a plant sample, and an animal sample.

* * * * *